(12) United States Patent
Fukuoka et al.

US007884251B2

(10) Patent No.: US 7,884,251 B2
(45) Date of Patent: Feb. 8, 2011

(54) INDUSTRIAL PROCESS FOR SEPARATING OUT BY-PRODUCED ALCOHOLS

(75) Inventors: Shinsuke Fukuoka, Tokyo (JP); Hironori Miyaji, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 342 days.

(21) Appl. No.: 11/660,900

(22) PCT Filed: Sep. 12, 2005

(86) PCT No.: PCT/JP2005/016708

§ 371 (c)(1), (2), (4) Date: Feb. 23, 2007

(87) PCT Pub. No.: WO2006/030724

PCT Pub. Date: Mar. 23, 2006

(65) Prior Publication Data

US 2008/0051595 A1   Feb. 28, 2008

(30) Foreign Application Priority Data

Sep. 17, 2004 (JP) .............................. 2004-272254

(51) Int. Cl.
C07C 27/10 (2006.01)

(52) U.S. Cl. .................. 568/700; 568/702; 558/270; 558/274; 558/277

(58) Field of Classification Search ................ 558/270, 558/274, 277; 568/700, 702
See application file for complete search history.

(56) References Cited

U.S. PATENT DOCUMENTS

| | | | |
|---|---|---|---|
| 4,182,726 A | 1/1980 | Illuminati et al. |
| 4,252,737 A | 2/1981 | Krimm et al. |
| 4,410,464 A | 10/1983 | Hallgren |
| 4,552,704 A | 11/1985 | Mark |
| 4,554,110 A | 11/1985 | Mark |
| 4,609,501 A | 9/1986 | Mark |
| 5,282,965 A | 2/1994 | Urairi et al. |
| 5,334,742 A | 8/1994 | Schon et al. |
| 5,344,954 A | 9/1994 | Schon et al. |
| 5,362,901 A | 11/1994 | Wagner et al. |
| 5,705,673 A | 1/1998 | Rivetti et al. |
| 5,747,609 A | 5/1998 | Komiya et al. |
| 6,262,210 B1 | 7/2001 | Tojo et al. |
| 6,767,517 B2 | 7/2004 | de Bruin et al. |

FOREIGN PATENT DOCUMENTS

| | | |
|---|---|---|
| EP | 0781760 A1 | 7/1997 |
| JP | 54-48732 A | 4/1979 |
| JP | 56-25138 A | 3/1981 |
| JP | 56-123948 A | 9/1981 |
| JP | 58-185536 A | 10/1983 |
| JP | 60-169444 A | 9/1985 |
| JP | 60-169445 A | 9/1985 |
| JP | 60-173016 A | 9/1985 |
| JP | 61-172852 A | 8/1986 |
| JP | 61-291545 A | 12/1986 |
| JP | 62-277345 A | 12/1987 |
| JP | 4-9358 A | 1/1992 |
| JP | 4-211038 A | 8/1992 |
| JP | 4-224547 A | 8/1992 |
| JP | 4-230242 A | 8/1992 |
| JP | 4-235951 A | 8/1992 |
| JP | 6-9506 A | 1/1994 |
| JP | 6-41022 A | 2/1994 |
| JP | 6-157410 A | 6/1994 |
| JP | 6-157424 A | 6/1994 |
| JP | 6-184058 A | 7/1994 |
| JP | 7-101908 A | 4/1995 |
| JP | 7-304713 A | 11/1995 |
| JP | 9-40616 A | 2/1997 |
| JP | 9-59225 A | 3/1997 |
| JP | 9-110805 A | 4/1997 |
| JP | 9-165357 A | 6/1997 |
| JP | 9-173819 A | 7/1997 |
| JP | 9-176094 A | 7/1997 |
| JP | 9-194436 A | 7/1997 |
| JP | 9-255772 A | 9/1997 |
| JP | 11-92429 A | 4/1999 |

(Continued)

*Primary Examiner*—Sudhakar Katakam
(74) *Attorney, Agent, or Firm*—Birch, Stewart, Kolasch & Birch, LLP

(57) ABSTRACT

It is an object of the present invention to provide a specific industrial separation process that enables an alcohol to be separated out efficiently and stably for a prolonged period of time from a large amount of a low boiling point reaction mixture containing a by-produced alcohol when mass-producing aromatic carbonates on an industrial scale by subjecting a dialkyl carbonate and an aromatic monohydroxy compound to transesterification reaction in a reactive distillation column in which a catalyst is present. Although there have been various proposals regarding processes for the production of aromatic carbonates by means of a reactive distillation method, these have all been on a small scale and short operating time laboratory level, and there have been no disclosures whatsoever on a specific process or apparatus enabling mass production on an industrial scale to be carried out stably for a prolonged period of time. Moreover, there have been no disclosures on a specific process or apparatus enabling the alcohol by-produced when producing aromatic carbonates the an industrial scale using a reactive distillation system to be separated out efficiently and stably for a prolonged period of time on an industrial scale of not less than 200 kg/hr. According to the present invention, there is proposed a specific process using a continuous multi-stage distillation column having a specified structure enabling the above object to be attained.

16 Claims, 3 Drawing Sheets

FOREIGN PATENT DOCUMENTS

| | | |
|---|---|---|
| JP | 2000-191596 A | 7/2000 |
| JP | 2000-191597 A | 7/2000 |
| JP | 2001-64234 A | 3/2001 |
| JP | 2001-64235 A | 3/2001 |
| JP | 2003-113144 A | 4/2003 |
| JP | 2003-155264 A | 5/2003 |
| JP | 2003-516374 A | 5/2003 |
| JP | 2003-291257 A | 10/2003 |
| JP | 2004-323384 A | 11/2004 |
| WO | WO-97/11049 A1 | 3/1997 |
| WO | WO 00/18720 * | 4/2000 |
| WO | WO-00/18720 A1 | 4/2000 |
| WO | WO-01/42187 A1 | 6/2001 |
| WO | WO-02/40439 A2 | 5/2002 |

* cited by examiner

INDUSTRIAL PROCESS FOR SEPARATING OUT BY-PRODUCED ALCOHOLS

TECHNICAL FIELD

The present invention relates to an industrial process for separating out by-produced alcohols. More particularly, the present invention relates to an industrial process for separating out the alcohols efficiently and stably for a prolonged period of time from a large amount of a low boiling point reaction mixture containing by-produced alcohols when mass-producing at least one aromatic carbonate on an industrial scale by subjecting a dialkyl carbonate and an aromatic monohydroxy compound to transesterification reaction in a reactive distillation column in which a catalyst is present.

BACKGROUND ART

Aromatic carbonate is important as a raw material for the production of an aromatic polycarbonate, which is the most widely used engineering plastics, without using toxic phosgene. As a process for producing an aromatic carbonate, a process of reacting an aromatic monohydroxy compound with phosgene has been known from long ago, and has also been the subject of a variety of studies in recent years. However, this process has the problem of using phosgene, and in addition chlorinated impurities that are difficult to separate out are present in the aromatic carbonate produced using this process, and hence the aromatic carbonate cannot be used in an application in which high purity is required, for example as a raw material for the production of an aromatic polycarbonate.

On the other hand, it is also known that a process for producing aromatic carbonates through transesterification reactions between a dialkyl carbonate and an aromatic monohydroxy compound. However, since such transesterification reactions are all equilibrium reactions and the equilibrium is biased extremely toward the original system, and the reaction rate is slow, and there have been many difficulties in producing aromatic carbonates industrially in large amounts using this method. In addition to development of catalysts being carried out, many attempts have thus been made to devise a reaction system so as to shift the equilibrium toward the product system as much as possible, and thus improve the aromatic carbonate yield. For example, for the reaction between dimethyl carbonate and phenol, there have been proposed a method in which by-produced methanol is distilled off by azeotropy together with an azeotrope-forming agent (see Patent Document 1: Japanese Patent Application Laid-Open No. 5448732 (corresponding to West German Patent Application No. 736063, and U.S. Pat. No. 4,252, 737)), and a method in which the by-produced methanol is removed by being adsorbed onto a molecular sieve (see Patent Document 2: Japanese Patent Application Laid-Open No. 58-185536 (corresponding to U.S. Pat. No. 410,464)). Moreover, a method has also been proposed in which, using an apparatus in which a distillation column is provided on top of a reactor, an alcohol by-produced in the reaction is separated off from the reaction mixture, and at the same time unreacted starting material that evaporates is separated off by distillation (see Patent Document 3-1: examples in Japanese Patent Application Laid-Open No. 56-123948 (corresponding to U.S. Pat. No. 4,182,726); Patent Document 3-2: examples in Japanese Patent Application Laid-Open No. 56-25138; Patent Document 3-3: examples in Japanese Patent Application Laid-Open No. 60-169444 (corresponding to U.S. Pat. No. 4,554,110); Patent Document 3-4: examples in Japanese Patent Application Laid-Open No. 60-169445 (corresponding to U.S. Pat. No. 4,552,704); Patent Document 3-5 examples in Japanese Patent Application Laid-Open No. 60-173016 (corresponding to U.S. Pat. No. 4,609,501); Patent Document 3-6: examples in Japanese Patent Application Laid-Open No. 61-172852; Patent Document 3-7: examples in Japanese Patent Application Laid-Open No. 61-291545; Patent Document 3-8: examples in Japanese Patent Application Laid-Open No. 62-277345).

However, these reaction systems have basically been batch system or switchover system. This is because the extent to which the reaction rate can be improved through catalyst development is limited for such a transesterification reaction, and hence the reaction rate is still slow, and thus it has been thought that a batch system is preferable to a continuous system. Of these, a continuous stirring tank reactor (CSTR) system in which a distillation column is provided on top of a reactor has been proposed as a continuous system, but there are problems such as the reaction rate being slow, and the gas-liquid interface in the reactor being small based on the volume of the liquid. It is thus not possible to make the conversion high. Accordingly, it is difficult to attain the object of producing an aromatic carbonate continuously in large amounts stably for a prolonged period of time by means of the above methods, and many issues remain to be resolved before economical industrial implementation is possible.

The present inventors have developed reactive distillation methods in which such a transesterification reaction is carried out in a continuous multi-stage distillation column simultaneously with separation by distillation, and have been the first in the world to disclose that such a reactive distillation system is useful for such a transesterification reaction, for example, a reactive distillation method in which a dialkyl carbonate and an aromatic hydroxy compound are continuously fed into the multi-stage distillation column, and the reaction is carried out continuously inside the column in which a catalyst is present, while continuously withdrawing a low boiling point component containing an alcohol produced as a by-product by distillation and continuously withdrawing a component containing a produced alkyl aryl carbonate from a lower portion of the column (see Patent Document 4: Japanese Patent Application Laid-Open No. 3-291257), a reactive distillation method in which an alkyl aryl carbonate is continuously fed into the multi-stage distillation column, and the reaction is carried out continuously inside the column in which a catalyst is present, while continuously withdrawing a low boiling point component containing a dialkyl carbonate produced as a by-product by distillation, and continuously withdrawing a component containing a produced diaryl carbonate from a lower portion of the column (see Patent document 5: Japanese Patent Application Laid-Open No. 4-9358), a reactive distillation method in which these reactions are carried out using two continuous multi-stage distillation columns, and hence a diaryl carbonate is produced continuously while efficiently recycling a dialkyl carbonate produced as a by-product (see Patent document 6: Japanese Patent Application Laid-Open No. 4-211038), and a reactive distillation method in which a dialkyl carbonate and an aromatic hydroxy compound or the like are continuously fed into the multi-stage distillation column, and a liquid that flows down through the column is withdrawn from a side outlet provided at an intermediate stage and/or a lowermost stage of the distillation column, and is introduced into a reactor provided outside the distillation column so as to bring about reaction, and is then introduced back through a circulating inlet provided at a stage above the stage where the outlet is provided, whereby reaction is carried out in both the reactor and the distillation column (see Patent Documents 7-1: Japanese Patent Application Laid-Open No. 4-224547; Patent Document 7-2: Japanese Patent Application Laid-Open No. 4-230242; Patent Document 7-3: Japanese Patent Application Laid-Open No. 4-235951).

These reactive distillation methods proposed by the present inventors are the first to enable aromatic carbonates to be produced continuously and efficiently, and many similar reactive distillation systems based on the above disclosures have been proposed thereafter (see Patent Document 8: Italian Patent No. 01255746; Patent Document 9: Japanese Patent Application Laid-Open No. 6-9506 (corresponding to European Patent No. 0560159, and U.S. Pat. No. 5,282,965); Patent Document 10: Japanese Patent Application Laid-Open No. 6-41022 (corresponding to European Patent No. 0572870, and U.S. Pat. No. 5,362,901); Patent Documents 11: Japanese Patent Application Laid-Open No. 6-157424 (corresponding to European Patent No. 0582931, and U.S. Pat. No. 5,334,742); Patent Document 12: Japanese Patent Application Laid-Open No. 6-184058 (corresponding to European Patent No. 0582930, and U.S. Pat. No. 5,344,954); Patent Document 13: Japanese Patent Application Laid-Open No. 7-304713; Patent Document 14: Japanese Patent Application Laid-Open No. 9-40616; Patent Document 15: Japanese Patent Application Laid-Open No. 9-59225; Patent Document 16: Japanese Patent Application Laid-Open No. 9-110805; Patent Document 17: Japanese Patent Application Laid-Open No. 9-165357; Patent Document 18: Japanese Patent Application Laid-Open No. 9-173819; Patent Documents 19-1: Japanese Patent Application Laid-Open No. 9-176094; Patent Document 19-2: Japanese Patent Application Laid-Open No. 2000-191596; Patent Document 19-3: Japanese Patent Application Laid-Open No. 2000-191597; Patent Documents 20: Japanese Patent Application Laid-Open No. 9-194436 (corresponding to European Patent No. 0785184, and U.S. Pat. No. 5,705,673); Patent Documents 21: International Publication No. 00/18720 (corresponding to U.S. Pat. No. 6,093,842); Patent Document 22-1: Japanese Patent Application Laid-Open No. 2001-64234; Patent Document 22-2: Japanese Patent Application Laid-Open No. 2001-64235; Patent Document 23: International Publication No. 02/40439 (corresponding to U.S. Pat. Nos. 6,596,894, 6,596,895, and 6,600,061)).

Among the reactive distillation systems, the present applicants have further proposed, a method carried out while keeping the weight ratio of a polyhydric aromatic hydroxy compound in the reaction system to a catalyst metal at not more than 2.0 (see Patent Document 24: International Publication No. 97/11049 (corresponding to European Patent No. 0855384,. and U.S. Pat. No. 5,872,275)), as a method that enables highly pure aromatic carbonates to be produced stably for a prolonged period of time without a large amount of a catalyst being required, a method in which a high boiling point material containing a catalyst component is reacted with an active substance and then separated off, and the catalyst component is recycled (see Patent Document 25: Japanese Patent Application Laid-Open No. 11-92429 (corresponding to European Patent No. 1016648, and U.S. Pat. No. 6,262,210)). Furthermore, the present inventors have also proposed a method in which 70 to 99% by weight of phenol produced as a by-product in a polymerization process is used as a starting material, and diphenyl carbonate can be produced by means of the reactive distillation method. This diphenyl carbonate can be used as the raw material for polymerization to produce aromatic polycarbonates (see Patent Documents 26: Japanese Patent Application Laid-Open No. 9-255772 (corresponding to European Patent No. 0892001, and U.S. Pat. No. 5,747,609)).

However, in all of these prior art documents in which the production of aromatic carbonates using the reactive distillation method is proposed, there is no disclosure whatsoever of a specific process or apparatus enabling mass production on an industrial scale (e.g. a more than 1 ton/hr), nor is there any description suggesting such a process or apparatus. For example, for the case of producing mainly methyl phenyl carbonate (MPC) from dimethyl carbonate and phenol, the maximum amount produced of methyl phenyl carbonate (MPC) disclosed in documents hitherto has been that disclosed in Patent Documents 24 and 25, but this amount is less than 10 kg/hr, which is not an amount produced on an industrial scale.

On the other hand, several proposals have also been made regarding processes for separating out the alcohols from a reaction mixture containing methanol by-produced through a transesterification reaction between dimethyl carbonate and phenol. For example, there have been proposed a process in which the above reaction is carried out using a reactor in which a liquid phase portion is divided into a plurality of reaction sections, and the reaction liquid passes through the sections in order and flows out from the reactor, and gas is withdrawn from a vapor phase portion, and subjected to heat exchange, before being subjected to separation in a distillation column (see Patent Document 27: Japanese Patent Application Laid-Open No. 2003-113144), and a process in which the same reactor is used, and the gas is withdrawn from the vapor phase portion, and subjected to heat exchange and thus liquefied, before being subjected to separation by distillation at a higher pressure than that of the pressure in the vapor phase portion of the reactor (see Patent Document 28: Japanese Patent Application Laid-Open No. 2003-155264). However, the object of these processes is to separate out the gas components with reduced energy consumption when carrying out reaction using a continuous stirring tank reactor as mentioned earlier as the reactor. Moreover, the composition of the gas components obtained using this reaction system is, for example, 98.1% by weight of dimethyl carbonate, 1.4% by weight of methanol, and 0.5% by weight of phenol, methyl phenyl carbonate and so on (See Patent Document 28), which differs greatly to the composition of a low boiling point reaction mixture containing a by-produced alcohol produced using a reactive distillation system. This is obviously different therefore to the case of separating out to a prescribed concentration the alcohol from a low boiling point reaction mixture produced using a reactive distillation system. A process has also been proposed in which a liquid containing approximately 10 to 74% by weight of methanol is distilled off at approximately 30 g/hr from the top of a distillation column provided on top of a tank reactor (see Patent Document 29: Japanese Patent Application Laid-Open No. 6-157410). However, the above patent documents either relate to processes carried out on a small amount laboratory scale, or else merely relate to carrying out a comparative calculation of the amount of energy required for the distillation. There is no specific description or suggestion whatsoever in any of the above patent documents relating to carrying out separation on an industrial scale.

In the case of carrying out transesterification reaction between the dialkyl carbonate and the aromatic hydroxy compound using the reactive distillation system, the by-produced alcohols are generally continuously withdrawn from an upper portion of the reactive distillation column as a low boiling point reaction mixture also containing compounds present in the reaction system having a lower boiling point than the at least one aromatic carbonate produced, for example the dialkyl carbonate and aromatic hydroxy compound constituting the starting material, a by-produced alkyl aryl ether and so on. Since this transesterification reaction is an equilibrium reaction having an extremely low equilibrium constant and the by-produced alcohols impede the reaction, in the case of industrial implementation, it thus becomes important to continuously carry out separation and recovery from the low boiling point reaction mixture into a component having a low content of the alcohol and a component containing mainly the alcohol efficiently and stably for a prolonged period of time.

Several proposals have been made regarding processes for carrying out separation by distillation of the low boiling point reaction mixture containing methanol and dimethyl carbonate withdrawn from an upper portion of a column when subjecting dimethyl carbonate and phenol to transesterification reaction using the reactive distillation system. These are an extractive distillation process in which the methanol is withdrawn from the top of the column while extracting the dimethyl carbonate using dimethyl oxalate as an extractant (see Patent Document 30: Japanese Patent Application Laid-Open No. 7-101908), an extractive distillation process in which the methanol is withdrawn from the top of the column while extracting the dimethyl carbonate using ethylene carbonate as an extractant (see Patent Document 14), a process in which distillation is carried out at normal pressure and a mixture containing approximately 70% by weight of methanol and approximately 30% by weight of dimethyl carbonate is obtained from the top of the column (see Patent Documents 19), a process in which a mixture containing 64.5% by weight of methanol and 35.5% by weight of dimethyl carbonate is obtained from the top of the column (see Patent Document 20), and a process in which a mixture containing 60 to 40% by weight of methanol and 40 to 60% by weight of dimethyl carbonate is obtained from the top of the column (see Patent Document 15).

However, with the extractive distillation processes, a large amount of the extractant must be used, and after the extraction, the extractant and the dimethyl carbonate must be further separated from one another. With the other processes, the content of the methanol in the liquid withdrawn from the top of the column is low at less than 80% by weight, and hence this is undesirable in the case of use as a raw material for producing dimethyl carbonate. Moreover, in the separation/recovery processes described in the above patent documents, the amount of methanol separated out and recovered is not more than a few hundreds of grams per hour. Even in Patent Document 20, which describes the largest amount, the amount of methanol processed is only approximately 0.9 kg/hr.

Furthermore, regarding the time for which the separating out of the methanol by distillation is carried out continuously in the above patent documents, the longest time in the case of Patent Document 29, in which the reaction system other than the reactive distillation system is used, is at most 720 hours. The longest time in the case that the reactive distillation system is used is only 2 weeks (Patent Document 19), with the others being 10 days (Patent Document 15), or the time taken for a steady state to be attained (Patent Documents 14 and 30). These periods of time are extremely short, and there is no disclosure or suggestion of an industrial separation process in which the distillation operation is carried out stably for a prolonged period of time of several thousand hours, for example 5000 hours.

In this way, for the case of industrially producing aromatic carbonates using the reactive distillation method, there has been no specific disclosure or suggestion whatsoever regarding an industrial process or apparatus for separating out a large amount of a by-produced alcohol efficiently and stably for a prolonged period of time.

DISCLOSURE OF INVENTION

It is an object of the present invention to provide a specific industrial separation process that enables an alcohol to be separated out efficiently and stably for a prolonged period of time from a large amount of a low boiling point reaction mixture containing a by-produced alcohol when mass-producing an aromatic carbonate on an industrial scale by subjecting a dialkyl carbonate and an aromatic monohydroxy compound to transesterification reaction in a reactive distillation column in which a catalyst is present.

Since the present inventors disclosed a process for producing aromatic carbonates using a continuous multi-stage distillation column, various proposals regarding processes for the production of aromatic carbonates by means of the reactive distillation method have been made. However, these have all been on a small scale and short operating time laboratory level, and there have been no disclosures whatsoever on a specific process or apparatus enabling mass production on an industrial scale. The present inventors thus carried out studies aimed at discovering a specific process enabling an alcohol by-produced when producing an aromatic carbonate on an industrial scale using the reactive distillation system to be separated out efficiently and stably for a prolonged period of time on an industrial scale of not less than 200 kg/hr. As a result, the present inventors have reached to the present invention.

That is, the present invention provides:

1. In an industrial process for separating out a by-produced alcohol in a case of continuously mass-producing an aromatic carbonate on an industrial scale using a reactive distillation system of continuously feeding a dialkyl carbonate and an aromatic monohydroxy compound into a continuous multi-stage distillation column A in which a catalyst is present and carrying out transesterification reaction and distillation simultaneously in the column A, comprising the steps of continuously withdrawing a low boiling point reaction mixture $A_T$ containing said by-produced alcohol from an upper portion of the column in a gaseous form, continuously feeding said low boiling point reaction mixture $A_T$ into a continuous multi-stage distillation column B, and carrying out separation by distillation into a low boiling point mixture $B_T$ having said by-produced alcohol as a main component thereof continuously withdrawn from an upper portion of the column in a gaseous form and a high boiling point mixture $B_B$ continuously withdrawn from a lower portion of the column in a liquid form, the improvement which comprises:

said continuous multi-stage distillation column B is a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (8):

$$500 \leq L_1 \leq 3000 \tag{1}$$

$$100 \leq D_1 \leq 500 \tag{2}$$

$$2 \leq L_1/D_1 \leq 30 \tag{3}$$

$$10 \leq n_1 \leq 40 \tag{4}$$

$$700 \leq L_2 \leq 5000 \tag{5}$$

$$50 \leq D_2 \leq 400 \tag{6}$$

$$10 \leq L_2/D_2 \leq 50 \tag{7}$$

$$35 \leq n_2 \leq 100 \tag{8}.$$

2. The process according to item 1, wherein said continuous multi-stage distillation column A comprises a structure having a pair of end plates above and below a cylindrical trunk portion having a length L (cm) and an inside diameter D (cm) and having an internal with a number of stages n thereinside, and comprises a gas outlet having an inside diameter $d_1$ (cm) at the top of the column or in an upper portion of the column near thereto, a liquid outlet having an inside diameter $d_2$ (cm) at the bottom of the column or in a lower portion of the column near thereto, at least one inlet provided in the upper portion and/or a central portion of the column below the gas outlet, and at least one inlet provided in the lower portion of the column above the liquid outlet, wherein L, D, L/D, n, $D/d_1$ and $D/d_2$ satisfy the following formulae:

$$1500 \leq L \leq 8000 \tag{9}$$

$$100 \leq D \leq 2000 \tag{10}$$

$$2 \leq L/D \leq 40 \tag{11}$$

$$20 \leq n \leq 120 \tag{12}$$

$$5 \leq D/d_1 \leq 30 \tag{13), and}$$

$$3 \leq D/d_2 \leq 20 \tag{14}.$$

3. The process according to the item 1 or 2, wherein a molar ration of the dialkyl carbonate fed into said continuous multi-stage distillation column A to the aromatic monohydroxy compound is in a range of from 0.5 to 3, a feeding amount of the aromatic monohydroxy compound is not less than 7 ton/hr, and an amount of the aromatic carbonate produced is not less than 1 ton/hr.
4. The process according to any one of items 1 to 3, wherein the reactive distillation in said continuous multi-stage distillation column A is carried out at a temperature of from 100 to 350° C. and at a pressure of from 0.1 Pa to $2 \times 10^7$ Pa.
5. The process according to any one of items 1 to 4, wherein the distillation conditions include a temperature of from 100 to 350° C. and a pressure of from $2 \times 10^5$ Pa to $5 \times 10^6$ Pa, and a reflux ratio of from 0.1 to 20.
6. The process according to any one of items 1 to 5, wherein a concentration of said alcohol in said low boiling point mixture $B_T$ is not less than 90% by weight, based on 100% by weight of said low boiling point mixture.
7. The process according to any one of items 1 to 6, wherein a content of said alcohol in said high boiling point mixture $B_B$ is not more than 0.2% by weight, based on 100% by weight of said high boiling point mixture.
8. The process according to any one of items 1 to 7, wherein an amount of said alcohol separated out is not less than 200 kg/hr.
9. The process according to any one of items 1 to 8, wherein $L_1, D_1, L_1/D_1, n_1, L_2, D_2, L_2/D_2$, and $n_2$ for said continuous multi-stage distillation column B satisfy the following formulae: $800 \leq L_1 \leq 2500$, $120 \leq D_1 \leq 400$, $5 \leq L_1/D_1 \leq 20$, $13 \leq n_1 \leq 25$, $1500 \leq L_2 \leq 3500$, $70 \leq D_2 \leq 200$, $15 \leq L_2/D_2 \leq 30$, $40 \leq n_2 \leq 70$, $L_1 \leq L_2$, and $D_2 \leq D_1$, respectively.
10. The process according to any one of items 1 to 9, wherein the internal in each of the stripping section and the enrichment section of said continuous multi-stage distillation column B is a tray and/or a packing.
11. The process according to item 10, wherein the internal in each of the stripping section and the enrichment section of said continuous multi-stage distillation column B is the tray.
12. The process according to any one of items 6 to 11, wherein the concentration of said alcohol in said low boiling point mixture $B_T$ is not less than 95% by weight, based on 100% by weight of said low boiling point mixture.
13. The process according to item 12, wherein the concentration of said alcohol in said low boiling point mixture $B_T$ is not less than 97% by weight, based on 100% by weight of said low boiling point mixture.
14. The process according to any one of items 7 to 13, wherein the content of said alcohol in said high boiling point mixture $B_B$ is not more than 0.1% by weight, based on 100% by weight of said high boiling point mixture.
15. The process according to any one of items 1 to 14, wherein said low boiling point mixture $B_T$ is used as a raw material for producing a dialkyl carbonate.
16. The process according to any one of items 1 to 15, wherein said high boiling point mixture $B_B$ is continuously fed into said continuous multi-stage distillation column A and thus used as a starting material for the transesterification.
17. The process according to any one of items 1 to 16, wherein heat in said low boiling point reaction mixture $A_T$ withdrawn in the gaseous form is used to heat the starting material for the transesterification reaction fed into said continuous multi-stage distillation column A.

ADVANTAGEOUS EFFECTS OF THE INVENTION

By implementing the present invention, when continuously mass-producing aromatic carbonates on an industrial scale using a reactive distillation system with a dialkyl carbonate and an aromatic monohydroxy compound as a starting material, a low boiling point reaction mixture ($A_T$) containing by-produced alcohols can be separated efficiently and stably for a prolonged period of time into a low boiling point mixture ($B_T$) in which the content of the alcohols is not less than 90% by weight and a high boiling point mixture ($B_B$) in which the content of the alcohols is not more than 0.2% by weight on a scale such that the amount of the alcohols separated out is not less than 200 kg/hr.

Figure 1:
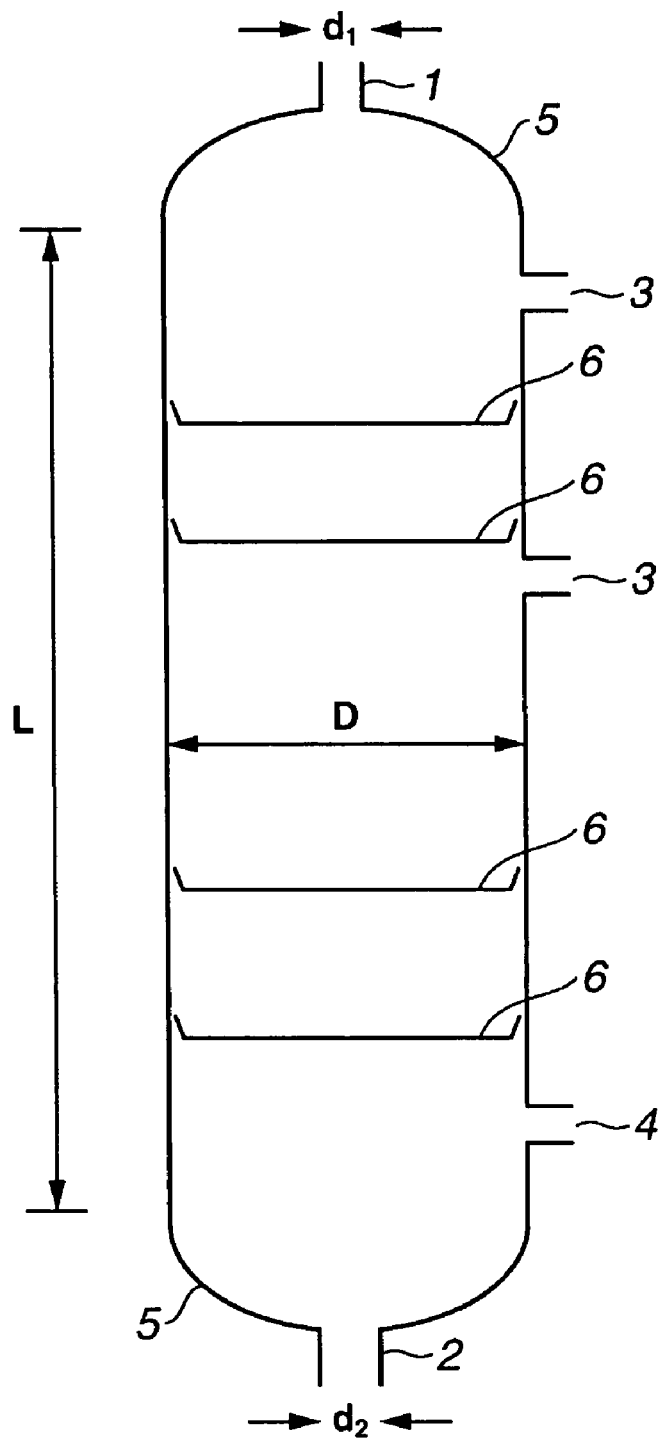
FIG. 1 is a schematic view of an example showing a continuous multi-stage distillation column A for carrying out reactive distillation in the present invention. The continuous multi-stage distillation column A comprises an internal (for example, a tray 6) installed therein, which has n stages.

1: gas outlet; 2: liquid outlet; 3 and 4: inlet; 5: end plate; 6, 7, 8: tray; SS: stripping section; ES: enrichment section; L: length (cm) of a continuous multi-stage distillation column A; D: inside diameter (cm) of the continuous multi-stage distillation column A; $d_1$: inside diameter (cm) of gas outlet of the continuous multi-stage distillation column A; $d_2$: inside diameter (cm) of liquid outlet of the continuous multi-stage distillation column A; $L_1$: length (cm) of the stripping section of the continuous multi-stage distillation column A; $L_2$: length (cm) of the enrichment section of the continuous multi-stage distillation column A; $D_1$: inside diameter (cm) of a stripping section of the continuous multi-stage distillation column B; $D_2$: inside diameter of an enrichment section of the continuous multi-stage distillation column B; 10, 11, 20, 21, 31, 41, 51: inlet; 22, 25, 32, 35, 39: liquid outlet; 26, 36: gas outlet; 24, 34, 38 inlet; 23, 33, 27, 37: heat exchanger.

BEST MODE FOR CARRYING OUT THE INVENTION

In the following, the present invention is described in detail.

A dialkyl carbonate used in the present invention is a compound represented by the general formula (15);

$$R^1OCOOR^1 \tag{15}$$

wherein $R^1$ represents an alkyl group having 1 to 10 carbon atoms, an alicyclic group having 3 to 10 carbon atoms, or an aralkyl group having 6 to 10 carbon atoms. Examples of $R^1$ include an alkyl group such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; an alicyclic group such as cyclopropyl, cyclobutyl, cyclopentyl, cyclohexyl and cycloheptyl; and an aralkyl group such as benzyl, phenethyl (isomers), phenylpropyl (isomers), phenylbutyl (isomers) and methylbenzyl (isomers). The above-mentioned alkyl groups, alicyclic group and aralkyl group may be substituted with other substituents such as Ia ower alkyl group, a lower alkoxy group, a cyano group or a halogen atom, and may also contain an unsaturated bond therein.

Examples of dialkyl carbonates having such $R^1$ include dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers) and di(cyanoethyl) carbonate (isomers).

Of these dialkyl carbonates, ones preferably used in the present invention are dialkyl carbonates in which $R^1$ is an alkyl group having not more than four carbon atoms and not containing a halogen atom. A particularly preferable one is dimethyl carbonate. Moreover, of preferable dialkyl carbonates, particularly preferable ones are dialkyl carbonates produced in a state substantially not containing a halogen, for example ones produced from an alkylene carbonate substantially not containing a halogen and an alcohol substantially not containing a halogen.

An aromatic monohydroxy compound used in the present invention is a compound represented by the following formula (16). The type of the aromatic monohydroxy compound is not limited, so long as the hydroxyl group is directly bonded to the aromatic group;

$$Ar^1OH \tag{16}$$

wherein $Ar^1$ represents an aromatic group having 5 to 30 carbon atoms. Examples of aromatic monohydroxy compounds having such $Ar^1$ include phenol; various alkylphenols such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols such as methoxyphenol (isomers) and ethoxyphenol (isomers); arylalkylphenols such as phenylpropylphenol (isomers); naphthol (isomers) and various substituted naphthols; and heteroaromatic monohydroxy compounds such as hydroxypyridine (isomers), hydroxycoumarin (isomers) and hydroxyquinoline (isomers). Of these aromatic monohydroxy compounds, ones preferably used in the present invention are unsubstituted and substituted phenols in which $Ar^1$ is an aromatic group having 6 to 10 carbon atoms. Phenol is particularly preferable. Moreover, of these aromatic monohydroxy compounds, ones substantially not containing a halogen are preferably used in the present invention.

Reactions in which alcohols are by-produced through transesterification reaction using a reactive distillation system in the present invention are shown in the following formulae (17) and (18). In the present invention, it is the reaction of formula (17) that mainly occurs.

$$R^1OCOOR^1 + Ar^1OH \rightarrow Ar^1OCOOR^1 + R^1OH \tag{17}$$

$$Ar^1OCOOR^1 + Ar^1OH \rightarrow Ar^1OCOOAr^1 + R^1OH \tag{18}$$

The molar ratio of the dialkyl carbonate to the aromatic monohydroxy compound used in the transesterification reaction in the present invention must be in a range of from 0.5 to 3. Outside this range, the amount of unreacted starting material remaining relative to a predetermined amount produced of the aromatic carbonate aimed for becomes high, which is not efficient, and moreover much energy is required to recover the aromatic carbonate. For such reasons, the above molar ratio is more preferably in a range of from 0.8 to 2.5, yet more preferably from 1.0 to 2.0.

In the transesterification reaction through a reactive distillation method using the continuous multi-stage distillation column A in the present invention, the aromatic carbonates are produced continuously on an industrial scale, for example in an amount of not less than 1 ton/hr. The minimum amount of the aromatic monohydroxy compound fed in continuously for the above production is generally 13 P ton/hr, preferably 10 P ton/hr, more preferably 7 P ton/hr, based on the amount of the aromatic carbonate (P ton/hr) to be produced. More preferably, this amount can be made to be less than 7 P ton/hr. In this case, the amount of the alcohols by-produced is generally not less than 0.2 P ton/hr.

The aromatic carbonates produced in the present invention include an alkyl aryl carbonate, or a diaryl carbonate, or a mixture thereof, which are obtained through the transesterification reaction between the dialkyl carbonate and the aromatic monohydroxy compound. Included under this transesterification reaction are a reaction in which one or both of the alkoxy groups of the dialkyl carbonate is/are exchanged with the aryloxy group of the aromatic monohydroxy compound and the alcohol is eliminated (formulae 17 and 18), and a reaction in which two molecules of the alkyl aryl carbonate produced are converted into the diaryl carbonate and the dialkyl carbonate through transesterification therebetween, i.e. disproportionation reaction (formula 19).

$$2Ar^1OCOOR^1 \rightarrow Ar^1OCOOAr^1 + R^1OCOOR^1 \qquad (19)$$

In the transesterification reaction in the present invention, although the alkyl aryl carbonate is mainly obtained, this alkyl aryl carbonate can be converted into the diaryl carbonate by being made to further undergo transesterification reaction with the aromatic monohydroxy compound, or disproportionation reaction (formula 19). This diaryl carbonate does not contain a halogen at all, and hence it is important as a raw material when industrially producing a polycarbonate by means of a transesterification method. Note that through the transesterification reaction in the present invention, a small amount of an alkyl aryl ether is generally produced as a reaction by-product.

The dialkyl carbonate and the aromatic monohydroxy compound used in the starting material in the transesterification reaction of the present invention may each be of high purity, or may contain other compounds, for example may contain compounds or reaction by-products produced in this process and/or another process. In the case of an industrial implementation, for the starting material, besides fresh dialkyl carbonate and aromatic monohydroxy compound newly introduced into the reaction system, it is also preferable to use dialkyl carbonate and aromatic monohydroxy compound recovered from this process and/or another process. In the process according to the present invention, a low boiling point reaction mixture ($A_T$) continuously withdrawn from an upper portion of the continuous multi-stage distillation column A in which reactive distillation is carried out is fed into a continuous multi-stage distillation column B; it is particularly preferable to return into the continuous multi-stage distillation column A a high boiling point mixture ($B_B$) continuously withdrawn from a lower portion of the continuous multi-stage distillation column B in a liquid form, whereby the high boiling point mixture ($B_B$) can be reused as a starting material for the transesterification reaction.

As a catalyst used in the transesterification reaction of the present invention, for example, a metal-containing compound selected from the following compounds can be used;

<Lead Compounds>:
lead oxides such as PbO, $PbO_2$ and $Pb_3O_4$; lead sulfides such as PbS and $Pb_2S$; lead hydroxides such as $Pb(OH)_2$ and $Pb_2O_2(OH)_2$; plumbites such as $Na_2PbO_2$, $K_2PbO_2$, $NaHPbO_2$ and $KHPbO_2$; plumbates such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof such as $PbCO_3$ and $2PbCO_3 \cdot Pb(OH)_2$; lead salts of organic acids, and carbonates and basic salts thereof, such as $Pb(OCOCH_3)_2$, $Pb(OCOCH_3)_4$ and $Pb(OCOCH_3)_2 \cdot PbO \cdot 3H_2O$, organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_3PbO$ (where Bu represents a butyl group, and Ph represents a phenyl group); alkoxylead compounds and aryloxylead compounds such as $Pb(OCH_3)_2$, $(CH_3O)Pb(OPh)$ and $Pb(OPh)_2$; lead alloys such as Pb—Na, Pb—Ca, Pb—Ba, Pb—Sn and Pb—Sb; lead minerals such as galena and zinc blende; and hydrates of such lead compounds;

<Copper Family Metal Compounds>:
salts and complexes of copper family metals such as CuCl, $CuCl_2$, CuBr, $CuBr_2$, CuI, $CuI_2$, $Cu(OAc)_2$, $Cu(acac)_2$, copper oleate, $Bu_2Cu$, $(CH_3O)_2Cu$, $AgNO_3$, AgBr, silver picrate, $AgC_6H_6ClO_4$, [AuC≡C—C(CH_3)_3]_n and $[Cu(C_7H_8)Cl]_4$ (wherein acac represents an acetylacetone chelate ligand);

<Alkali Metal Complexes>:
alkali metal complexes such as Li(acac) and $LiN(C_4H_9)_2$;

<Zinc Complexes>:
zinc complexes such as $Zn(acac)_2$;

<Cadmium Complexes>:
cadmium complexes such as $Cd(acac)_2$;

<Iron Family Metal Compounds>:
complexes of iron family metals such as $Fe(C_{10}H_8)(CO)_5$, $Fe(CO)_5$, $Fe(C_4H_6)(CO)_3$, $Co(mesitylene)_2$, $(PEt_2Ph_2)$, $CoC_5F_5(CO)_7$, Ni-$\pi$-$C_5H_5NO$ and ferrocene;

<Zirconium Complexes>:
zirconium complexes such as $Zr(acac)_4$ and zirconocene;

<Lewis Acid Type Compounds>:
Lewis acids and Lewis acid-forming transition metal compounds such as $AlX_3$, $TiX_3$, $TiX_4$, $VOX_3$, $VX_5$, $ZnX_2$, $FeX_3$ and $SnX_4$ (wherein X represents a halogen atom, an acetoxy group, an alkoxy group or an aryloxy group); and <Organotin Compounds>:
organotin compounds such as $(CH_3)_3SnOCOCH_3$, $(C_2H_5)_3SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(OCH_3)_2$, $(C_2H_5)_3SnOH$, $Ph_3SnOH$, $Bu_2SnO$, $(C_8H_{17})_2SnO$, $Bu_2SnCl_2$ and BuSnO(OH).

Each of these catalysts may be a solid catalyst fixed inside the multi-stage distillation column, or may be a soluble catalyst that dissolves in the reaction system.

Each of these catalyst components may of course have been reacted with an organic compound present in the reaction system such as an aliphatic alcohol, the aromatic monohydroxy compound, the alkyl aryl carbonate, the diaryl carbonate or the dialkyl carbonate, or may have been subjected to heating treatment with the starting material or the products prior to the reaction.

In the case of carrying out the present invention with a soluble catalyst which dissolves in the reaction system, the catalyst is preferably one having a high solubility in the reaction liquid under the reaction conditions. Examples of preferable catalysts in this sense include PbO, $Pb(OH)_2$ and $Pb(OPh)_2$; $TiCl_4$, $Ti(OMe)_4$, $(MeO)Ti(OPh)_3$, $(MeO)_2Ti(OPh)_2$, $(MeO)_3Ti(OPh)$ and $Ti(OPh)_4$; $SnCl_4$, $Sn(OPh)_4$, $Bu_2SnO$ and $Bu_2Sn(OPh)_2$; $FeCl_3$, $Fe(OH)_3$ and $Fe(OPh)_3$; or such catalysts which have been treated with phenol, the reaction liquid or the like.

In the present invention, a method of making the catalyst be present in the continuous multi-stage distillation column A may be any method, but in the case that the catalyst is a solid that is insoluble in the reaction liquid, there is, for example, a method in which the catalyst is fixed inside the continuous multi-stage distillation column A by, for example, being installed on a plate inside the column or being installed in the form of a packing. In the case of a catalyst that dissolves in the starting material or the reaction liquid, it is preferable to feed the catalyst into the distillation column A from a position above the central portion of the distillation column. In this case, the catalyst liquid dissolved in the starting material or reaction liquid may be introduced into the column together with the starting material, or may be introduced into the column from a different inlet to the starting material. The amount of the catalyst used in the present invention varies depending on the type thereof, the types and proportions of the starting material compounds, and reaction conditions such as the reaction temperature and the reaction pressure. The amount of the catalyst is generally in a range of from 0.0001 to 30% by weight, preferably from 0.005 to 10% by weight, more preferably from 0.001 to 1% by weight based on the total weight of the starting material.

FIG. 1 is a schematic view of an example showing a continuous multi-stage distillation column A for carrying out reactive distillation in the present invention. The continuous multi-stage distillation column A used as the reactive distillation column in the present invention may be any continuous multi-stage distillation column so long as at least one aromatic carbonate can be produced stably for a prolonged period of time on an industrial scale, for example in an amount of not less than 1 ton/hr. For example, a continuous multi-stage distillation column which comprises a structure having a length L (cm), an inside diameter D (cm), and an internal (for example, tray 6) with a number of stages n thereinside, and which has a gas outlet having an inside diameter $d_1$ (cm) at the top of the column or in an upper portion of the column near to the top, a liquid outlet having an inside diameter $d_2$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein L, D, n, $d_1$, and $d_2$ satisfy the following formulae (9) to (14), is particularly preferable:

$$1500 \leq L \leq 8000 \quad (9)$$

$$100 \leq D \leq 2000 \quad (10)$$

$$2 \leq L/D \leq 40 \quad (11)$$

$$20 \leq n \leq 120 \quad (12)$$

$$5 \leq D/d_1 \leq 30 \quad (13)$$

$$3 \leq D/d_2 \leq 20 \quad (14).$$

It should be noted that the term "in an upper portion of the column near to the top" refers to the portion extending downwardly from the top of the column to the location measuring about 0.25 L, and the term "in a lower portion of the column near to the bottom" refers to the portion extending upwardly from the bottom of the column to the location measuring about 0.25 L. Note that L is defined above.

By using the continuous multi-stage distillation column A that simultaneously satisfies formulae (9) to (14) as the reactive distillation column, the aromatic carbonate can be produced on an industrial scale of not less than 1 ton/hr, generally 1 to 100 ton/hr, with high selectivity and high productivity stably for a prolonged period of time, for example not less than 2000 hours, preferably not less than 3000 hours, more preferably not less than 5000 hours, from the dialkyl carbonate and the aromatic monohydroxy compound.

The reaction time for the transesterification reaction carried out in the present invention is considered to equate to the average residence time of the reaction liquid in the continuous multi-stage distillation column A. The reaction time varies depending on the form of the internal in the distillation column and the number of stages, the amount of the starting material fed into the column, the type and amount of the catalyst, the reaction conditions and so on. The reaction time is generally in a range of from 0.01 to 10 hours, preferably 0.05 to 5 hours, more preferably 0.1 to 3 hours. The reaction temperature varies depending on the type of the starting material compounds used, and the type and amount of the catalyst, but is generally in a range of from 100 to 350° C. It is preferable to increase the reaction temperature so as to increase the reaction rate. However, if the reaction temperature is too high, then side reactions become liable to occur, for example production of by-products such as an alkyl aryl ether increases, which is undesirable. For this reason, the reaction temperature is preferably in a range of from 130 to 280° C., more preferably 150 to 260° C., yet more preferably 180 to 250° C. Moreover, the reaction pressure varies depending on the type of the starting material compounds used and the composition of the starting material, the reaction temperature and so on. The reaction pressure may be any of a reduced pressure, normal pressure, or an applied pressure. The reaction pressure is generally in a range of from 0.1 to $2 \times 10^7$ Pa, preferably $10^5$ to $10^7$ Pa, more preferably $2 \times 10^5$ to $5 \times 10^6$ Pa.

When carrying out the present invention, the aromatic carbonates are continuously produced by continuously feeding the dialkyl carbonate and aromatic monohydroxy compound constituting the starting material into the continuous multi-stage distillation column A in which the catalyst is present and carrying out reaction and distillation simultaneously in the column, continuously withdrawing the low boiling point reaction mixture ($A_T$) containing the by-produced alcohols from the upper portion of the column in a gaseous form, and continuously withdrawing a high boiling point reaction mixture containing the aromatic carbonates from the lower portion of the column in a liquid form. In the case that not less than 1 ton/hr of the aromatic carbonates are produced, not less than approximately 200 kg/hr of the alcohols are generally by-produced. Together with compounds present in the reaction system having a lower boiling point than that of the aromatic carbonate, the by-produced alcohols are continuously withdrawn from the upper portion of the continuous multi-stage distillation column A as the low boiling point reaction mixture ($A_T$), and continuously fed into the continuous multi-stage distillation column B and continuously subjected to separation by distillation therein. A low boiling point mixture ($B_T$) having the alcohols as a main component thereof is continuously withdrawn from an upper portion of the column B in a gaseous form, while a high boiling point mixture ($B_B$) is continuously withdrawn from a lower portion of the column B. The low boiling point reaction mixture ($A_T$) may of course contain small amounts of the aromatic carbonate and compounds having a higher boiling point than that of the aromatic carbonate.

In the present invention, the amount of the low boiling point reaction mixture ($A_T$) continuously withdrawn from the continuous multi-stage distillation column A varies depending on the composition and amount of the starting material, the reactive distillation conditions, the conversion, the selectivity and so on, but is generally from 10 ton/hr to 1000 ton/hr, preferably 20 ton/hr to 800 ton/hr, more preferably from 30 ton/hr to 500 ton/hr. The composition of the low boiling point reaction mixture ($A_T$) subjected to the separation in the present invention varies depending on the reactive distillation conditions for the continuous multi-stage distillation column A, the composition of the recycled starting material and so on, but is generally 1.5 to 10% by weight of the by-produced alcohol, 50 to 85% by weight of the dialkyl carbonate, 10 to 40% by weight of the aromatic monohydroxy compound, 0.5 to 10% by weight of the by-product alkyl aryl ether, 0 to 5% by weight of the aromatic carbonate, and 0 to 3% by weight of other material.

Figure 2:
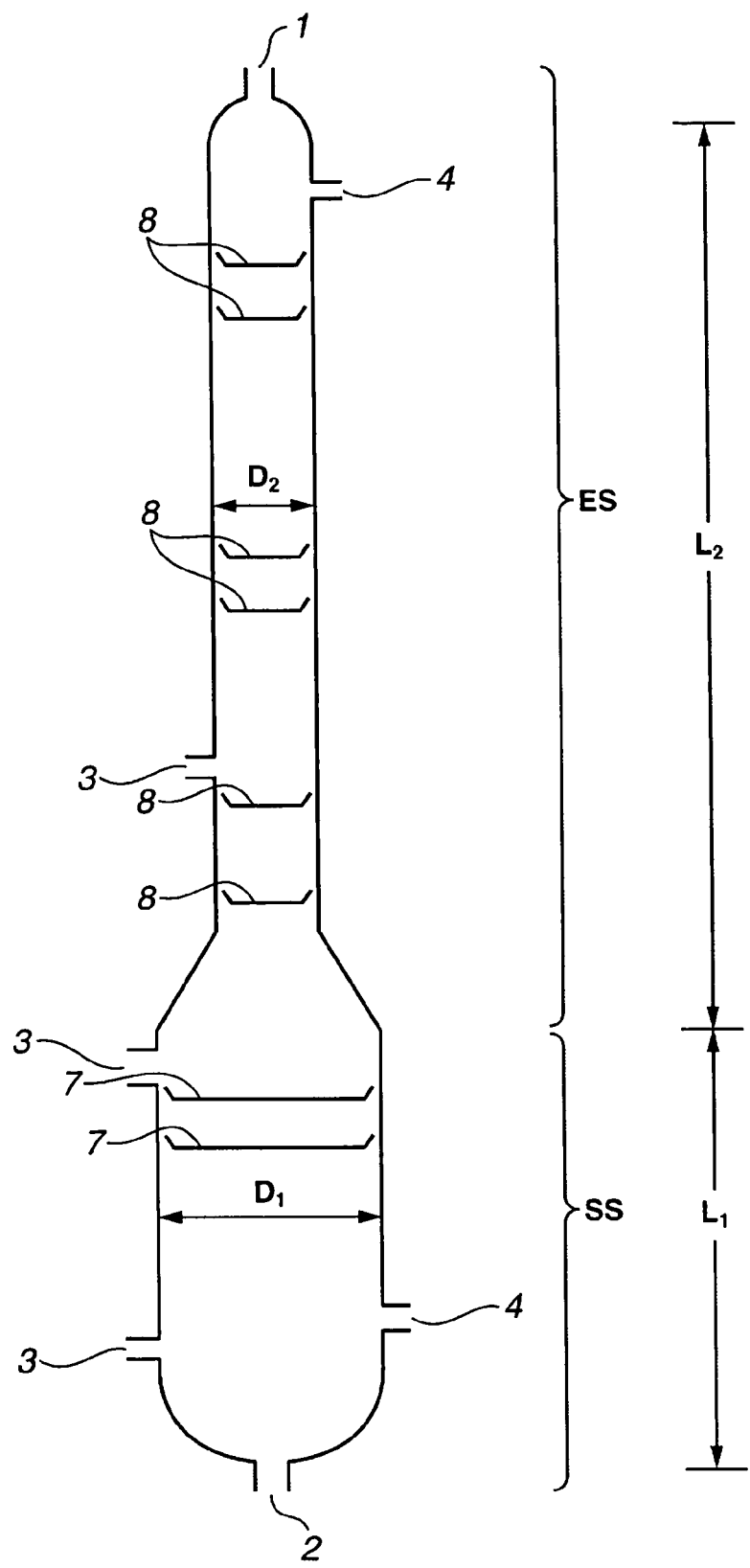
FIG. 2 is a schematic view of an example showing a continuous multi-stage distillation column B for carrying out separation by distillation on a low boiling point reaction mixture ($A_T$) containing an alcohol in the present invention. The continuous multi-stage distillation column B comprises an internal installed therein, wherein the number of stages of the internals is $n_1$ in a stripping section (for example, a tray 7) and $n_2$ in an enrichment section (for example, a tray 8), respectively.

FIG. 2 is a schematic view of an example showing a continuous multi-stage distillation column B for carrying out separation by distillation on a low boiling point reaction mixture ($A_T$) with the above composition. The continuous multi-stage distillation column B used in the present invention must be a distillation column comprising a stripping section SS having a length $L_1$ (cm), an inside diameter $D_1$ (cm) and an internal (for example, tray 7) with a number of stages $n_1$ thereinside, and an enrichment section ES having a length $L_2$ (cm), an inside diameter $D_2$ (cm) and an internal (for example, tray 8) with a number of stages $n_2$ thereinside, wherein $L_1$, $D_1$, $n_1$, $L_2$, $D_2$, and $n_2$ satisfy the following formulae (1) to (8):

$$500 \leq L_1 \leq 3000 \quad (1)$$

$$100 \leq D_1 \leq 500 \quad (2)$$

$$2 \leq L_1/D_1 \leq 30 \quad (3)$$

$$10 \leq n_1 \leq 40 \quad (4)$$

$$700 \leq L_2 \leq 5000 \quad (5)$$

$$50 \leq D_2 \leq 400 \quad (6)$$

$$10 \leq L_2/D_2 \leq 50 \quad (7)$$

$$35 \leq n_2 \leq 100 \quad (8).$$

Note that reference is made to the drawings in which the same reference numbers are used through the different figures to designate the same members.

It has been ascertained that by using such a continuous multi-stage distillation column, it is easy to make the amount of the alcohols separated out be not less than 200 kg/hr, with the concentration of the alcohols in the low boiling point mixture ($B_T$) being not less than 90% by weight, and the content of the alcohols in the high boiling point mixture ($B_B$) being not more than 0.2% by weight. The reason why a process for separating out the by-produced alcohols on an industrial scale with such excellent effects has become possible is not clear, but this is supposed to be due to a combined effect brought about when the conditions of formulae (1) to (8) are combined. Preferable ranges for the respective factors are described below.

If $L_1$ (cm) is less than 500, then the separation efficiency for the stripping section decreases, and hence the desired separation efficiency cannot be attained. Moreover, to keep down the equipment cost while securing the desired separation efficiency, $L_1$ must be made to be not more than 3000. A more preferable range for $L_1$ (cm) is $800 \leq L_1 \leq 2500$, with $1000 \leq L_1 \leq 2000$ being yet more preferable.

If $D_1$ (cm) is less than 100, then it is not possible to attain the desired distillation amount. Moreover, to keep down the equipment cost while attaining the desired distillation amount, $D_1$ must be made to be not more than 500. A more preferable range for $D_1$ (cm) is $120 \leq D_1 \leq 400$, with $150 \leq D_1 \leq 300$ being yet more preferable.

If $L_1/D_1$ is less than 2 or greater than 30, then prolonged stable operation becomes difficult. A more preferable range for $L_1/D_1$ is $5 \leq L_1/D_1 \leq 20$, with $7 \leq L_1/D_1 \leq 15$ being yet more preferable.

If $n_1$ is less than 10, then the separation efficiency for the stripping section decreases and hence the desired separation efficiency cannot be attained. Moreover, to keep down the equipment cost while securing the desired separation efficiency, $n_1$ must be made to be not more than 40. A more preferable range for $n_1$ is $13 \leq n_1 \leq 25$, with $15 \leq n_1 \leq 20$ being yet more preferable.

If $L_2$ (cm) is less than 700, then the separation efficiency for the enrichment section decreases, and hence the desired separation efficiency cannot be attained. Moreover, to keep down the equipment cost while securing the desired separation efficiency, $L_2$ must be made to be not more than 5000. Furthermore, if $L_2$ is greater than 5000, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $L_2$ (cm) is $1500 \leq L_2 \leq 3500$, with $2000 \leq L_2 \leq 3000$ being yet more preferable.

If $D_2$ (cm) is less than 50, then it is not possible to attain the desired distillation amount. Moreover, to keep down the equipment cost while attaining the desired distillation amount, $D_2$ must be made to be not more than 400. A more preferable range for $D_2$ (cm) is $70 \leq D_2 \leq 200$, with $80 \leq D_2 \leq 150$ being yet more preferable.

If $L_2/D_2$ is less than 10 or greater than 50, then prolonged stable operation becomes difficult. A more preferable range for $L_2/D_2$ is $15 \leq L_2/D_2 \leq 30$, with $20 \leq L_2/D_2 \leq 28$ being yet more preferable.

If $n_2$ is less than 35, then the separation efficiency for the enrichment section decreases and hence the desired separation efficiency cannot be attained. Moreover, to keep down the equipment cost while securing the desired separation efficiency, $n_2$ must be made to be not more than 100. Furthermore, if $n_2$ is greater than 100, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $n_2$ is $40 \leq n_2 \leq 70$, with $45 \leq n_2 \leq 65$ being yet more preferable.

Further, in the continuous multi-stage distillation column A, it is preferable for L, D, L/D, n, $D/d_1$, and $D/d_2$ for the continuous multi-stage distillation column A satisfy the following formulae; $2000 \leq L \leq 6000$, $150 \leq D \leq 1000$, $3 \leq L/D \leq 30$, $30 \leq n \leq 100$, $8 \leq D/d_1 \leq 25$, and $5 \leq D/d_2 \leq 18$, respectively, more preferably, $2500 \leq L \leq 5000$, $200 \leq D \leq 800$, $5 \leq L/D \leq 15$, $40 \leq n \leq 90$, $10 \leq D/d_1 \leq 25$, and $7 \leq D/d_2 \leq 15$, respectively. Furthermore, the relationship between $L_1$ and $L_2$, and the relationship between $D_1$ and $D_2$ vary depending on the amount of the low boiling point reaction mixture ($A_T$) fed into the continuous multi-stage distillation column B, the concentration of the alcohol and so on, but when carrying out the process of the present invention, preferably $L_1 \leq L_2$, and $D_2 \leq D_1$.

In the present invention, the continuous multi-stage distillation column A used as the reactive distillation column is preferably a distillation column having a tray and/or a packing as an internal. The continuous multi-stage distillation column B used for separating out the by-produced alcohols is preferably a distillation column having a tray and/or a packing as an internal in each of the stripping section and the enrichment section. The term "internal" used in the present invention means the parts in each distillation column where gas and liquid are actually brought into contact with one another. As the tray, for example, a bubble-cap tray, a sieve tray, a valve tray, a counterflow tray, a Superfrac tray, a Maxfrac tray or the like are preferable. As the packing, an irregular packing such as a Raschig ring, a Lessing ring, a Pall ring, a Berl saddle, an Intalox saddle, a Dixon packing, a McMahon packing or Heli-Pak, or a structured packing such as Mellapak, Gempak, TECHNO-PAK, Flexipac, a Sulzer packing, a Goodroll packing or a Glitchgrid are preferable. The multi-stage distillation column having both a tray portion and a portion packed with the packing can also be used. Note that the term "number of stages (n) of an internal" used in the present invention means that the total number of trays in the case of a tray, and the theoretical number of stages in the case of the packing. Accordingly, in the case of the multi-stage column having both the tray portion and the portion packed with the packing, n means the sum of the total number of trays and the theoretical number of stages of the packing.

In the present invention, it is particularly preferable for the internal in each of the stripping section and the enrichment section of the continuous multi-stage distillation column B to be the tray.

It has been discovered that, because the reaction between the dialkyl carbonate and the aromatic monohydroxy compound in the present invention has an extremely low equilibrium constant and the reaction rate is slow, it is particularly preferable for the continuous multi-stage distillation column A used for the reactive distillation to be a plate-type distillation column having the tray as the internal. Furthermore, it has been discovered that a sieve tray having a sieve portion and a down corner portion is particularly preferable as the tray in terms of the relationship between performance thereof and the equipment cost. It has been also discovered that the sieve tray preferably has 100 to 1000 holes/m$^2$ in the sieve portion. A more preferable number of holes is 120 to 900 holes/m$^2$, yet more preferably 150 to 800 holes/m$^2$. Moreover, it was discovered that the cross-sectional area per hole of the sieve tray is preferably in a range of from 0.5 to 5 cm$^2$. A more preferable cross-sectional area per hole is 0.7 to 4 cm$^2$, yet more preferably 0.9 to 3 cm$^2$. Furthermore, it has been discovered that it is particularly preferable if the sieve tray has 100 to 1000 holes/m$^2$ in the sieve portion, and the cross-sectional area per hole is in a range of from 0.5 to 5 cm$^2$. It has been shown that by adding the above conditions to the continuous multi-stage distillation column A, the object of the present invention can be attained more easily. Moreover, it has been discovered that when the internal of the continuous multi-stage distillation column B is the tray, this tray comprises a sieve tray which has the similar number of holes/m$^2$ and the similar cross-sectional area per hole as the tray of the continuous multi-stage distillation column A.

When carrying out the present invention, the dialkyl carbonate and aromatic monohydroxy compound constituting the starting material are continuously fed into the continuous multi-stage distillation column A in which the catalyst is present and reaction and distillation are carried out simultaneously in the column, and the high boiling point reaction mixture containing the aromatic carbonates is continuously withdrawn from the lower portion of the column in a liquid form, whereby the aromatic carbonates are continuously produced on an industrial scale. On the other hand, the low boiling point reaction mixture ($A_T$) containing the by-produced alcohols is continuously withdrawn from the upper portion of the column in a gaseous form. The low boiling point reaction mixture ($A_T$) is continuously fed into the continuous multi-stage distillation column B, the low boiling point mixture ($B_T$) containing the alcohols as a main component thereof is continuously withdrawn from the upper portion of the column in a gaseous form, and the high boiling point mixture ($B_B$) is continuously withdrawn from the lower portion of the column in a liquid form. When being fed into the continuous multi-stage distillation column B, the low boiling point reaction mixture ($A_T$) may be fed in as a gas, or as a liquid. Moreover, it is particularly preferable to use heat in the low boiling point reaction mixture ($A_T$), which is withdrawn from the continuous multi-stage distillation column in a gaseous form, to heat another material, for example the starting material for the transesterification fed into the continuous multi-stage distillation column A. In this case, depending on the extent to which the heat exchange is carried out, the low boiling point reaction mixture ($A_T$) fed into the continuous multi-stage distillation column B may be in a gaseous form, or a mixed gaseous/liquid form, or a liquid form. It is also preferable to heat or cool the low boiling point reaction mixture ($A_T$) to a temperature close to the temperature of the liquid in the vicinity of the inlet of the continuous multi-stage distillation column B before feeding the low boiling point reaction mixture ($A_T$) into the distillation column B.

Moreover, the position from which the low boiling point reaction mixture ($A_T$) is fed into the continuous multi-stage distillation column B is between the stripping section and the enrichment section. The continuous multi-stage distillation column B preferably comprises a reboiler for heating the distillate, and a refluxing apparatus.

In the present invention, the low boiling point reaction mixture ($A_T$) generally withdrawn from the continuous multi-stage distillation column A in an amount of 10 to 1000 ton/hr, is fed into the continuous multi-stage distillation column B and thus subjected to the separation by distillation, whereupon the low boiling point mixture ($B_T$) is continuously withdrawn from the upper portion of the distillation column B, and the high boiling point mixture ($B_B$) is continuously withdrawn from the lower portion of the distillation column B.

In the present invention, the concentration of the alcohols in the low boiling point mixture ($B_T$) must be made to be not less than 90% by weight, preferably not less than 95% by weight, more preferably not less than 97% by weight. Moreover, the content of the alcohols in the high boiling point mixture ($B_B$) can be made to be not more than 0.2% by weight, preferably not more than 0.1% by weight. Furthermore, the alcohols separated out as the main component of the low boiling point mixture ($B_T$) can be continuously separated out stably for a prolonged period of time in an amount of not less than 200 kg/hr, preferably not less than 500 kg/hr, more preferably 1 to 20 ton/hr.

In the present invention, the low boiling point mixture ($B_T$) separated off contains not less than 90% by weight of the by-produced alcohols. All or most of the remainder of the low boiling point mixture ($B_T$) is dialkyl carbonate. It is thus preferable to use the low boiling point mixture ($B_T$) as a raw material for dialkyl carbonate production. As processes for producing a dialkyl carbonate, a process using a carbonylation reaction of alcohols, and a process using an alcoholysis reaction of an alkylene carbonate are carried out industrially. The low boiling point mixture ($B_T$) can be used as a raw material for either of these reactions. Since the alcoholysis reaction of the alkylene carbonate is an equilibrium reaction, it is preferable to use a raw material having a high alcohol concentration. It is thus preferable to use the low boiling point mixture ($B_T$) obtained in the present invention as the raw material of such a reaction. In this case, the low boiling point mixture ($B_T$) having an alcohol concentration of not less than 95% by weight, more preferably not less than 97% by weight, is particularly preferably used as the raw material.

Moreover, the high boiling point mixture ($B_B$) separated off in the present invention contains the components of the low boiling point reaction mixture ($A_T$) minus those withdrawn as the low boiling point mixture ($B_T$). The high boiling point mixture ($B_B$) contains not more than 0.2% by weight, preferably not more than 0.1% by weight, of the by-produced alcohols, and generally has the dialkyl carbonate and the aromatic monohydroxy compound as main components thereof, while also containing a small amount of the by-produced alkyl aryl ether and a small amount of the aromatic carbonate. In the present invention, it is thus particularly preferable to continuously feed the high boiling point mixture ($B_B$) into the continuous multi-stage distillation column A, and thus use the high boiling point mixture ($B_B$) as a starting material 2 for the transesterification. In this case, in order to continue the reactive distillation at a steady state in the continuous multi-stage distillation column A, the amount of the dialkyl carbonate in the starting material 2 fed into the continuous multi-stage distillation column A is deficient with just that in the high boiling point mixture ($B_B$), and hence it is generally necessary to add fresh starting material containing the dialkyl carbonate in an amount commensurate with the deficiency. The starting material containing the dialkyl carbonate freshly added into the continuous multi-stage distillation column A may be fed into the continuous multi-stage distillation column A directly, or may be fed into the continuous multi-stage distillation column B and thus then fed into the continuous multi-stage distillation column A as part of the high boiling point mixture ($B_B$). In the case that this freshly added starting material containing the dialkyl carbonate contains the alcohol in a greater amount than, for example, 0.1% by weight, it is preferable for this starting material to be fed into the continuous multi-stage distillation column B from a suitable position thereof so as to reduce the content of the alcohol, and to then be fed into the continuous multi-stage distillation column A as part of the high boiling point mixture ($B_B$).

It should be noted that the starting material fed into the continuous multi-stage distillation column A contains a starting material 1 and the starting material 2. Typically, the starting material 1 contains a dialkyl carbonate which has been mainly produced by the disproportionation reaction (formula (19)) of the alkyl aryl carbonate separately. Accordingly, in the continuous multi-stage distillation column A, about a half amount of the dialkyl carbonate which has been consumed by the reaction in which the alkyl aryl carbonate is produced is made up for by adding the dialkyl carbonate into the starting material 1, which is produced by the above disproportionation reaction and is recycled. It is necessary to add a fresh dialkyl carbonate as the half amount of the dialkyl carbonate being deficient. This enables the reactive distillation to continue at the steady state. In the present invention, the above deficiency can be generally made up for by adding the fresh dialkyl carbonate into the starting material 2, but the above deficiency can also be made up for by adding the fresh dialkyl carbonate into the starting material 1.

The distillation conditions for the continuous multi-stage distillation column B used in the present invention are a column bottom temperature in a range of from 150 to 300° C., preferably 170 to 270° C., more preferably 190 to 250° C., and a column top pressure in a range of from $2 \times 10^5$ Pa to $5 \times 10^6$ Pa, preferably $4 \times 10^5$ Pa to $3 \times 10^6$ Pa, more preferably $6 \times 10^5$ Pa to $2 \times 10^6$ Pa. A reflux ratio in the continuous multi-stage distillation column B is generally in a range of from 0.1 to 20, preferably from 0.5 to 15, more preferably from 1.0 to 10.

The term "prolonged stable operation" used in the present invention means that the continuous multi-stage distillation column A for carrying out the reactive distillation and the continuous multi-stage distillation column B for carrying out the separation by distillation on the low boiling point reaction mixture ($A_T$) can each be operated continuously in a steady state based on the operating conditions with no flooding, clogging of piping, or erosion for not less than 1000 hours, preferably not less than 3000 hours, more preferably not less than 5000 hours, and a predetermined amount of the aromatic carbonate can be produced while maintaining a predetermined reaction yield and selectivity, and moreover a predetermined amount of the by-produced alcohols of not less than 200 kg/hr can be separated out by distillation while maintaining a predetermined separation efficiency.

The material constituting the continuous multi-stage distillation columns used in the present invention is generally a metallic material such as carbon steel or stainless steel. In terms of the quality of the aromatic carbonate produced, stainless steel is preferable for the continuous multi-stage distillation column A, and either carbon steel or stainless steel is preferable for the continuous multi-stage distillation column B.

EXAMPLES

Hereinbelow, the present invention will be described in more detail with reference to the following Examples, but the present invention is not limited to the following Examples. A composition of each mixture was measured by means of a gas chromatography method, and a halogen content was measured by means of an ion chromatography method.

Example 1

<Continuous Multi-stage Distillation Column A>

A continuous multi-stage distillation column as shown in FIG. 1 having L=3300 cm, D=500 cm, L/D=6.6, n=80, $D/d_1$=17, and $D/d_2$=9 was used. In this Example, a sieve tray was used as the internal, which has the cross-sectional area per hole being approximately 1.5 cm² and the number of holes being approximately 250/m².

<Continuous Multi-stage Distillation Column B>

A continuous multi-stage distillation column as shown in FIG. 2 having $L_1$=1700 cm, $D_1$=180 cm, $L_1/D_1$=9.4, $n_1$=16, $L_2$=2500 cm, $D_2$=100 cm, $L_2/D_2$=25, and $n_2$=55 was used. In this Example, a sieve tray (the cross-sectional area per hole being approximately 1.3 cm² and the number of holes being approximately 550/m²) was used as the internal in both the stripping section and the enrichment section.

<Reactive Distillation, and Separating Out of By-produced Methanol from Low Boiling Point Reaction Mixture ($A_T$)>

Figure 3:
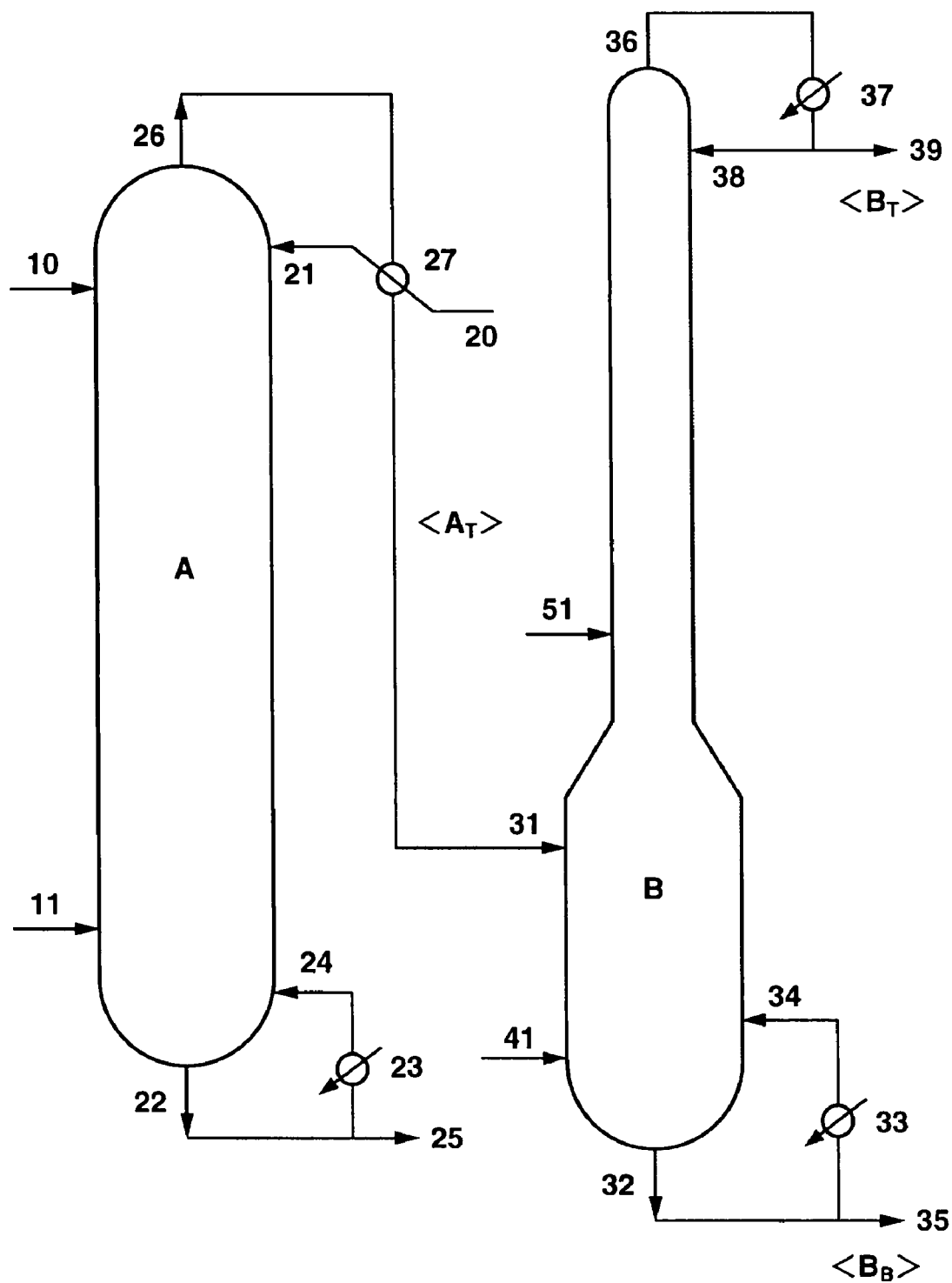
FIG. 3 is a schematic view of an example showing an apparatus for carrying out reactive distillation and distillation to separate out by-produced alcohols in the present invention.

Reactive distillation, and separating out of by-produced methanol were carried out using the apparatus shown in FIG. 3.

A starting material 1 containing 44% by weight of dimethyl carbonate, 49% by weight of phenol, 5.7% by weight of anisole, 1% by weight of methyl phenyl carbonate, and 0.3% by weight of methanol was continuously introduced into the continuous multi-stage distillation column A in a liquid form at a flow rate of 80.8 ton/hr from an upper portion inlet 21 of the continuous multi-stage distillation column A. Note that the starting material 1 was introduced from an inlet 20, and was fed in through the inlet 21 after having been heated using a heat exchanger 27 with heat from a low boiling point reaction mixture ($A_T$) withdrawn in a gaseous form from the upper portion of the distillation column A.

On the other hand, a starting material 2 containing 76% by weight of dimethyl carbonate, 19.5% by weight of phenol, 4.4% by weight of anisole, and 0.1% by weight of methyl phenyl carbonate was continuously introduced into the distillation column A at a flow rate of 86 ton/hr from a lower portion inlet 11 of the distillation column A. The molar ratio for the starting materials introduced into the continuous multi-stage distillation column A was dimethyl carbonate/phenol=1.87. The starting materials substantially did not contain halogens (outside the detection limit for the ion chromatography, i.e. 1 ppb or less). Pb(OPh)₂ as a catalyst was introduced into from an inlet 10 in the upper portion of the distillation column A such that a concentration thereof in the reaction liquid would be approximately 70 ppm. Reactive distillation was carried out continuously under conditions of a temperature at the bottom of the distillation column A being 233° C. and a pressure at the top of the distillation column A being $9.6 \times 10^5$ Pa. It was possible to attain stable steady state operation after 24 hours. A liquid continuously withdrawn at 82.3 ton/hr from an outlet 25 connected to the bottom of the distillation column A contained 10.1% by weight of methyl phenyl carbonate and 0.27% by weight of diphenyl carbonate. It was found that the amount of methyl phenyl carbonate produced was 8.3 ton/hr (subtracting the amount introduced into the distillation column A, the actual amount produced was 7.5 ton/hr), and the amount of diphenyl carbonate produced was 0.22 ton/hr. The total selectivity for the methyl phenyl carbonate and diphenyl carbonate based on the phenol reacted was 99%.

Prolonged continuous operation was carried out under these conditions. The amounts produced per hour at 500 hours, 2000 hours, 4000 hours, 5000 hours, and 6000 hours after attaining stable steady state were 8.3 tons, 8.3 tons, 8.3 tons, 8.3 tons, and 8.3 tons respectively for the methyl phenyl carbonate, and 0.22 tons, 0.22 tons, 0.22 tons, 0.22 tons, and 0.22 tons respectively for the diphenyl carbonate. The total selectivities for the methyl phenyl carbonate and diphenyl carbonate were 99%, 99%, 99%, 99%, and 99% respectively, and hence the operation was very stable. Moreover, the aromatic carbonates produced substantially did not contain halogens (1 ppb or less).

The low boiling point reaction mixture ($A_T$) continuously withdrawn in a gaseous form from the top of the continuous multi-stage distillation column A was cooled down to 170° C. through heat therein being used to heat the starting material 1 using the heat exchanger 27 as described above. The composition of the low boiling point reaction mixture ($A_T$), which was withdrawn at 85.2 ton/hr, was 2% by weight of methanol, 74% by weight of dimethyl carbonate, 19.5% by weight of phenol, 4.4% by weight of anisole, and 0.1% by weight of methyl phenyl carbonate. After being made to have a temperature close to the temperature of the liquid in the vicinity of an inlet 31 provided between the stripping section and the enrichment section in the continuous multi-stage distillation column B, the low boiling point reaction mixture ($A_T$) was continuously fed into the distillation column B from the inlet 31. On the other hand, in order to make up for the deficient dimethyl carbonate, fresh dimethyl carbonate was continuously introduced into the distillation column B at 2.53 ton/hr from an inlet 41 provided in the lower portion of the distillation column B. Separation by distillation was carried out continuously in the distillation column B at a column bottom temperature being 226° C., a column top temperature being 155° C., and a reflux ratio of 3. A low boiling point mixture ($B_T$) was continuously withdrawn from an outlet 39 at 1.73 ton/hr, while a high boiling point mixture ($B_B$) was continuously withdrawn from an outlet 35 at 86 ton/hr. The high boiling point mixture ($B_B$) had a methanol content of not more than 0.1% by weight, and had a composition the same as the starting material 2 for the continuous multi-stage distillation column A described above, and was circulated back and thus reused as the starting material 2.

The composition of the low boiling point mixture ($B_T$) was 97% by weight of methanol, and 3% by weight of dimethyl carbonate. The amount of methanol continuously separated out through the distillation was 1.68 ton/hr. The low boiling point mixture ($B_T$) was used as a raw material for producing dimethyl carbonate and ethylene glycol by reacting with ethylene carbonate.

The operation of the continuous multi-stage distillation column B was carried out in synchronization with the continuous operation of the continuous multi-stage distillation column A. The separation efficiency was the same after 500 hours, 2000 hours, 4000 hours, 5000 hours, and 6000 hours as initially, and hence operation remained stable.

Example 2

Reactive distillation, and separating out of by-produced methanol were carried out under the following conditions using the same continuous multi-stage distillation column A and continuous multi-stage distillation column B as in Example 1.

<Reactive Distillation>

A starting material 1 containing 33.3% by weight of dimethyl carbonate, 58.8% by weight of phenol, 6.8% by weight of anisole, 0.9% by weight of methyl phenyl carbonate, and 0.2% by weight of methanol was continuously introduced into the continuous multi-stage distillation column A in a liquid form at a flow rate of 86.2 ton/hr through the upper portion inlet 21 of the continuous multi-stage distillation column A via the heat exchanger 27 from the inlet 20. On the other hand, a starting material 2 containing 64.4% by weight of dimethyl carbonate, 33.8% by weight of phenol, 1.3% by weight of anisole, 0.4% by weight of methyl phenyl carbonate, and 0.1% by weight of methanol was continuously introduced into the distillation column A at a flow rate of 86.6 ton/hr from the lower portion inlet 11 of the distillation column A. The molar ratio for the starting materials introduced into the continuous multi-stage distillation column A was dimethyl carbonate/phenol=1.1. The starting materials substantially did not contain halogens (outside the detection limit for the ion chromatography, i.e. 1 ppb or less). Pb(OPh)$_2$ as a catalyst was introduced into from the upper portion inlet 10 of the distillation column A such that a concentration thereof in the reaction liquid would be approximately 100 ppm. Reactive distillation was carried out continuously under conditions of a temperature at the bottom of the distillation column A being 230° C. and a pressure at the top of the distillation column A being $6.5 \times 10^5$ Pa. It was possible to attain stable steady state operation after 24 hours. A liquid continuously withdrawn at 88 ton/hr from the outlet 25 connected to the bottom of the distillation column A contained 13.4% by weight of methyl phenyl carbonate and 0.7% by weight of diphenyl carbonate. It was found that the amount of methyl phenyl carbonate produced was 11.8 ton/hr (subtracting the amount introduced into the distillation column A, the actual amount produced was 10.7 ton/hr), and the amount of diphenyl carbonate produced was 0.6 ton/hr. The total selectivities for the methyl phenyl carbonate and diphenyl carbonate based on the phenol reacted was 98%.

Prolonged continuous operation was carried out under these conditions. The amounts produced per hour at 500 hours, 1000 hours, and 2000 hours after attaining stable steady state were 11.8 tons, 11.8 tons, and 11.8 tons respectively for the methyl phenyl carbonate, and 0.6 tons, 0.6 tons, and 0.6 tons respectively for the diphenyl carbonate. The total selectivities for the methyl phenyl carbonate and diphenyl carbonate were 98%, 98%, and 98% respectively, and hence the operation was very stable. Moreover, the aromatic carbonates produced substantially did not contain halogens (1 ppb or less).

<Separating Out of By-Produced Methanol from Low Boiling Point Reaction Mixture ($A_T$)>

The low boiling point reaction mixture ($A_T$) continuously withdrawn in a gaseous form from the top of the continuous multi-stage distillation column A was cooled down to 161° C. through heat therein being used to heat the starting material 1 using the heat exchanger 27 as described above. The composition of the low boiling point reaction mixture ($A_T$), which was withdrawn at 85.4 ton/hr, was 3.1% by weight of methanol, 61% by weight of dimethyl carbonate, 34.3% by weight of phenol, 1.2% by weight of anisole, and 0.2% by weight of methyl phenyl carbonate. After being made to have a temperature close to the temperature of the liquid in the vicinity of the inlet 31 provided between the stripping section and the enrichment section in the continuous multi-stage distillation column B, the low boiling point reaction mixture ($A_T$) was continuously fed into the distillation column B from the inlet 31. On the other hand, in order to make up for the deficient dimethyl carbonate, fresh dimethyl carbonate was continuously introduced into the distillation column B at 3.98 ton/hr from an inlet 51 provided at the fourth stage from the bottom of the enrichment section. Separation by distillation was carried out continuously in the distillation column B at a column bottom temperature being 213° C., a column top temperature being 138° C., and a reflux ratio of 2.89. A low boiling point mixture ($B_T$) was continuously withdrawn from the outlet 39 at 2.78 ton/hr, while a high boiling point mixture ($B_B$) was continuously withdrawn from the outlet 35 at 86.6 ton/hr. The high boiling point mixture ($B_B$) had a methanol content of not more than 0.1% by weight, and had a composition substantially the same as the starting material 2 for the continuous multi-stage distillation column A described above, and was circulated back and thus reused as the starting material 2.

The composition of the low boiling point mixture ($B_T$) was 93.3% by weight of methanol, and 6.7% by weight of dimethyl carbonate. The amount of methanol continuously separated out through the distillation was 2.59 ton/hr. The low boiling point mixture ($B_T$) was used as a raw material for producing dimethyl carbonate and ethylene glycol by reacting with ethylene carbonate.

The operation of the continuous multi-stage distillation column B was carried out in synchronization with the continuous operation of the continuous multi-stage distillation column A. The separation efficiency was the same after 500 hours, 1000 hours, and 2000 hours as initially, and hence operation remained stable.

Example 3

Reactive distillation was carried out using a similar process and the same continuous multi-stage distillation column A as in Example 1, and a low boiling point reaction mixture ($A_T$) containing 1.5% by weight of methanol, 81.9% by weight of dimethyl carbonate, 12.4% by weight of phenol, 3.9% by weight of anisole, and 0.3% by weight of methyl phenyl carbonate was withdrawn at 80.26 ton/hr from the upper portion outlet 26 of the column. As in Example 1, the low boiling point reaction mixture ($A_T$) was continuously fed into the continuous multi-stage distillation column B from the inlet 31 provided between the stripping section and the enrichment section of the continuous multi-stage distillation column B via the heat exchanger 27. On the other hand, in order to make up for the deficient dimethyl carbonate, fresh starting material containing 99% by weight of dimethyl carbonate and 1% by weight of methanol was continuously introduced into the distillation column B at 1.76 ton/hr from the inlet 51 provided at the fourth stage from the bottom of the enrichment section. Separation by distillation was carried out continuously in the distillation column B at a column bottom temperature being 219° C., a column top temperature being 151° C., and a reflux ratio of 6.74. A low boiling point mixture ($B_T$) was continuously withdrawn from the outlet 39 at 1.19 ton/hr, while a high boiling point mixture ($B_B$) was continuously withdrawn from the outlet 35 at 80.83 ton/hr. The high boiling point mixture ($B_B$) had a methanol content of not more than 0.1% by weight, and was circulated back into the continuous multi-stage distillation column A and thus reused as starting material for the reactive distillation.

The composition of the low boiling point mixture ($B_T$) was 99% by weight of methanol, and 1% by weight of dimethyl carbonate. The amount of methanol continuously separated out through the distillation was 1.18 ton/hr. The low boiling point mixture ($B_T$) was used as a raw material for producing dimethyl carbonate and ethylene glycol by reacting with ethylene carbonate.

The operation of the continuous multi-stage distillation column B was carried out in synchronization with the continuous operation of the continuous multi-stage distillation column A. The separation efficiency was the same after 500 hours, 1000 hours, and 2000 hours as initially, and hence operation remained stable.

Example 4

Reactive distillation was carried out using a similar process and the same continuous multi-stage distillation column A as in Example 1, and a low boiling point reaction mixture ($A_T$) containing 2.8% by weight of methanol, 61.0% by weight of dimethyl carbonate, 26.4% by weight of phenol, 9.6% by weight of anisole, and 0.2% by weight of methyl phenyl carbonate was withdrawn at 57.45 ton/hr from the upper portion outlet 26 of the column. As in Example 1, the low boiling point reaction mixture ($A_T$) was continuously fed into the continuous multi-stage distillation column B from the inlet 31 provided between the stripping section and the enrichment section of the continuous multi-stage distillation column B via the heat exchanger 27. On the other hand, in order to make up for the deficient dimethyl carbonate, fresh starting material containing 99.7% by weight of dimethyl carbonate and 0.3% by weight of methanol was continuously introduced into the distillation column B at 2.44 ton/hr from the inlet 51 provided at the fourth stage from the bottom of the enrichment section. Separation by distillation was carried out continuously in the distillation column B at a column bottom temperature being 215° C., a column top temperature being 138° C., and a reflux ratio of 4.4. A low boiling point mixture ($B_T$) was continuously withdrawn from the outlet 39 at 1.69 ton/hr, while a high boiling point mixture ($B_B$) was continuously withdrawn from the outlet 35 at 58.2 ton/hr. The high boiling point mixture ($B_B$) had a methanol content of 0.08% by weight, and was circulated back into the continuous multi-stage distillation column A and thus reused as starting material for the reactive distillation.

The composition of the low boiling point mixture ($B_T$) was 94.9% by weight of methanol, and 5.1% by weight of dimethyl carbonate. The amount of methanol continuously separated out through the distillation was 1.6 ton/hr. The low boiling point mixture ($B_T$) was used as a raw material for producing dimethyl carbonate and ethylene glycol by reacting with ethylene carbonate.

The operation of the continuous multi-stage distillation column B was carried out in synchronization with the continuous operation of the continuous multi-stage distillation column A. The separation efficiency was the same after 500 hours and 1000 hours as initially, and hence operation remained stable.

Example 5

Reactive distillation was carried out using a similar process and the same continuous multi-stage distillation column A as in Example 1, and a low boiling point reaction mixture ($A_T$) containing 3.0% by weight of methanol, 62.8% by weight of dimethyl carbonate, 28.0% by weight of phenol, 6.1% by weight of anisole, and 0.1% by weight of methyl phenyl carbonate was withdrawn at 57.11 ton/hr from the upper portion outlet 26 of the column. As in Example 1, the low boiling point reaction mixture ($A_T$) was continuously fed into the continuous multi-stage distillation column B from the inlet 31 provided between the stripping section and the enrichment section of the continuous multi-stage distillation column B via the heat exchanger 27. On the other hand, in order to make up for the deficient dimethyl carbonate, fresh dimethyl carbonate was continuously introduced into the distillation column B at 2.8 ton/hr from the inlet 51 provided at the fourth stage from the bottom of the enrichment section. Separation by distillation was carried out continuously in the distillation column B at a column bottom temperature being 213° C., a column top temperature being 138° C., and a reflux ratio of 2.89. A low boiling point mixture ($B_T$) was continuously withdrawn from the outlet 39 at 1.84 ton/hr, while a high boiling point mixture ($B_B$) was continuously withdrawn from the outlet 35 at 58.07 ton/hr. The high boiling point mixture ($B_B$) had a methanol content of 0.09% by weight, and was circulated back into the continuous multi-stage distillation column A and thus reused as starting material for the reactive distillation.

The composition of the low boiling point mixture. ($B_T$) was 93.3% by weight of methanol, and 6.7% by weight of dimethyl carbonate. The amount of methanol continuously separated out through the distillation was 1.72 ton/hr. The low boiling point mixture ($B_T$) was used as a raw material for producing dimethyl carbonate and ethylene glycol by reacting with ethylene carbonate.

The operation of the continuous multi-stage distillation column B was carried out in synchronization with the continuous operation of the continuous multi-stage distillation column A. The separation efficiency was the same after 500 hours, 1000 hours, and 2000 hours as initially, and hence operation remained stable.

INDUSTRIAL APPLICABILITY

The present invention can be suitably used as a specific industrial separation process that enables an alcohol to be separated out efficiently and stably for a prolonged period of time from a large amount of a low boiling point reaction mixture containing a by-produced alcohol when mass-producing aromatic carbonates on an industrial scale by subjecting a dialkyl carbonate and an aromatic monohydroxy compound to transesterification reaction in a reactive distillation column in which a catalyst is present.

We claim:

1. A process for separating out a by-produced alcohol in a case of continuously mass-producing an alkyl aryl carbonate mainly on an industrial scale using a reactive distillation system of continuously feeding a dialkyl carbonate and an aromatic monohydroxy compound into a continuous multi-stage distillation column A in which a catalyst is present and carrying out transesterification reaction and distillation simultaneously in the column A, comprising the steps of continuously withdrawing a low boiling point reaction mixture $A_T$ containing 1.5 to 10% by weight of said by-produced alcohol, 50 to 85% by weight of the dialkyl carbonate and 10 to 40% by weight of the aromatic monohydroxy compound from an upper portion of the column in a gaseous form, continuously feeding said low boiling point reaction mixture $A_T$ into a continuous multi-stage distillation column B, and carrying out separation by distillation into a low boiling point mixture $B_T$ having not less than 90% by weight of said by-produced alcohol and all or most of the remainder of the low boiling point mixture $B_T$ being dialkyl carbonate continuously withdrawn from an upper portion of the column in a gaseous form and a high boiling point mixture $B_B$ continuously withdrawn from a lower portion of the column in a liquid form, which comprises:

said continuous multi-stage distillation column B is a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (8):

$$500 \leq L_1 \leq 3000 \quad (1)$$

$$100 \leq D_1 \leq 500 \quad (2)$$

$$2 \leq L_1/D_1 \leq 30 \quad (3)$$

$$10 \leq n_1 \leq 40 \quad (4)$$

$$700 \leq L_2 \leq 5000 \quad (5)$$

$$50 \leq D_2 \leq 400 \quad (6)$$

$$10 \leq L_2/D \leq 50 \quad (7)$$

$$35 \leq n_2 \leq 100 \quad (8)$$

wherein an amount of said alcohol separated out is not less than 200 kg/hr.

2. The process according to claim 1, wherein said continuous multi-stage distillation column A comprises a structure having a pair of end plates above and below a cylindrical trunk portion having a length L (cm) and an inside diameter D (cm) and having an internal with a number of stages n thereinside, and comprises a gas outlet having an inside diameter $d_1$ (cm) at the top of the column or in an upper portion of the column near thereto, a liquid outlet having an inside diameter $d_2$ (cm) at the bottom of the column or in a lower portion of the column near thereto, at least one inlet provided in the upper portion and/or a central portion of the column below the gas outlet, and at least one inlet provided in the lower portion of the column above the liquid outlet, wherein L, D, L/D, n, D/$d_1$ and D/$d_2$ satisfy the following formulae:

$$1500 \leq L \leq 8000 \quad (9)$$

$$100 \leq D \leq 2000 \quad (10)$$

$$2 \leq L/D \leq 40 \quad (11)$$

$$20 \leq n \leq 120 \quad (12)$$

$$5 \leq D/d_1 \leq 30 \quad (13), and$$

$$3 \leq D/d_2 \leq 20 \quad (14).$$

3. The process according to the claim 1 or 2, wherein a molar ration of the dialkyl carbonate fed into said continuous multi-stage distillation column A to the aromatic mohohydroxy compound is in a range of from 0.5 to 3, a feeding amount of the aromatic monohydroxy compound is not less than 7 ton/hr, and an amount of the aromatic carbonate produced is not less than 1 ton/hr.

4. The process according to claim 1, wherein the reactive distillation in said continuous multi-stage distillation column A is carried out at a temperature of from 100 to 350° C. and at a pressure of from 0.1 Pa to $2 \times 10^7$ Pa.

5. The process according to claim 1, wherein the distillation conditions of said continuous multi-stage distillation column B include a temperature of from 100 to 350° C. and a pressure of from $2 \times 10^5$ Pa to $5 \times 10^6$ Pa, and a reflux ratio of from 0.1 to 20.

6. The process according to claim 1, wherein a concentration of said alcohol in said low boiling point mixture $B_T$ is not less than 90% by weight, based on 100% by weight of said low boiling point mixture.

7. The process according to claim 1, wherein a content of said alcohol in said high boiling point mixture $B_B$ is not more than 0.2% by weight, based on 100% by weight of said high boiling point mixture.

8. The process according to claim 1, wherein $L_1$, $D_1$, $L_1/D_1$, $n_1$, $L_2$, $D_2$, $L_2/D_2$, and $n_2$ for said continuous multi-stage distillation column B satisfy the following formulae: $800 \leq L_1 \leq 2500$, $120 \leq D \leq 400$, $5 \leq L_1/D_1 \leq 20$, $13 \leq n_1 \leq 25$, $1500 \leq L_2 \leq 3500$, $70 \leq D_2 \leq 200$, $15 \leq L_2/D_2 \leq 30$, $40 \leq n_2 \leq 70$, $L_1 \leq L_2$, and $D_2 \leq D_1$, respectively.

9. The process according to claim 1, wherein the internal in each of the stripping section and the enrichment section of said continuous multi-stage distillation column B is a tray and/or a packing.

10. The process according to claim 9, wherein the internal in each of the stripping section and the enrichment section of said continuous multi-stage distillation column B is the tray.

11. The process according to claim 6, wherein the concentration of said alcohol in said low boiling point mixture $B_T$ is not less than 95% by weight, based on 100% by weight of said low boiling point mixture.

12. The process according to claim 11, wherein the concentration of said alcohol in said low boiling point mixture $B_T$ is not less than 97% by weight, based on 100% by weight of said low boiling point mixture.

13. The process according to claim 7, wherein the content of said alcohol in said high boiling point mixture $B_B$ is not more than 0.1% by weight, based on 100% by weight of said high boiling point mixture.

14. The process according to claim 1, wherein said low boiling point mixture $B_T$ is used as a raw material for producing a dialkyl carbonate.

15. The process according to claim 1, wherein said high boiling point mixture $B_B$ is continuously fed into said continuous multi-stage distillation column A and thus used as a starting material for the transesterification.

16. The process according to claim 1, wherein heat in said low boiling point reaction mixture $A_T$ withdrawn in the gaseous form is used to heat the starting material for the transesterification reaction fed into said continuous multi-stage distillation column A.

* * * * *